(12) United States Patent
Dennis et al.

(10) Patent No.: US 8,404,005 B2
(45) Date of Patent: Mar. 26, 2013

(54) METHODS AND SYSTEMS FOR IMPROVED BIODIESEL PRODUCTION

(75) Inventors: Brian H. Dennis, Arlington, TX (US); Richard E. Billo, Colleyville, TX (US); Christopher R. Oliver, Commerce Township, MI (US); John W. Priest, Dallas, TX (US); Edward S. Kolesar, Ft. Worth, TX (US); Elinor Kolesar, legal representative, Ft. Worth, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 376 days.

(21) Appl. No.: 12/556,857

(22) Filed: Sep. 10, 2009

(65) Prior Publication Data
US 2011/0060152 A1 Mar. 10, 2011

(51) Int. Cl.
*C10L 1/18* (2006.01)
*C11C 3/04* (2006.01)

(52) U.S. Cl. ............ 44/308; 44/307; 554/169; 554/167; 554/170

(58) Field of Classification Search .................. None
See application file for complete search history.

(56) References Cited

U.S. PATENT DOCUMENTS
6,129,973 A * 10/2000 Martin et al. ................. 428/166
2009/0165366 A1 * 7/2009 Jovanovic et al. ............... 44/308

FOREIGN PATENT DOCUMENTS
WO   WO2007/142983   * 12/2007

OTHER PUBLICATIONS

Guan, G. et al., Transesterificatin of Sunflower oil with methanol in a microtube reactor, Jan. 7, 2009, Ind. ENg. Chem. Res, vol. 48, No. 3, pp. 1357-1363.*
Jachuck, R. et al., Green engineering: continuous production of biodiesel using an alkaline catalyst in an intensified narrow channel reactor, Jan. 13, 2009, Journal of Environmental Monitoring, 11, pp. 642-647.*
Wen, Z. et al., Intensification of biodiesel synthesis using zigzag micro-channel reactors, Feb. 20, 2009, Bioresource Technology, 100, pp. 3054-3060.*
Charoenwat, R. et al., Transesterification of vegetable oils with a cintinuous flow capillary reactor, Apr. 17-18, 2009, 2009 ETC proceedings, ASME early career technical conference, (5 pages).*
Tanthapanichakoon, W. et al., Design of mixing in microfluidic liquid slugs based on a new dimesionless number for precise reacton and mixing operations, 2006, Chemical Engineering Science, vol. 61, pp. 4220-4232.*

(Continued)

*Primary Examiner* — Yate K Cutliff
(74) *Attorney, Agent, or Firm* — Chowdhury & Georgakis, P.C.

(57) ABSTRACT

In a method and system to produce biodiesel using an improved catalytic transesterification process, a first reactant and a second reactant are dispersed to form a laminar slug flow pattern within a microchannel of a microreactor, the first reactant and the second reactant being immiscible. The first reactant and the second reactant are mixed, thereby triggering a reaction between them to produce the biodiesel and glycerol, the mixing being convection-enhanced by shear stress induced circulation occurring within each slug of the reactants. The reaction takes place under a pressure that is less than 5 psi and under a temperature that is less than 70 degrees Celsius. Separation of the glycerol from the biodiesel occurs simultaneously with the mixing. Several microreactors are coupled in parallel to improve throughput of the biodiesel.

25 Claims, 9 Drawing Sheets

OTHER PUBLICATIONS

Dennis, B.H. et al., Inverse detrminatin of kinetic rate constants for transesterification of vegetable oils, 2008, Inverse Problems in Science and Engineering, vol. 16, No. 6, pp. 693-704.*

Tice, J.D., et al., Formaiton of droplets and mixing in multiphase microfluidics at low values of the Reynolds and the capillary numbers, 2003, Langmuir, vol. 19, No. 22, pp. 9127-9133.*

DuPont, Viton fluoroelastomer, 2012, abstract, 1 page.*

Jon Van Gerpen, "Biodiesel Processing and Production", Fuel Processing Technology, vol. 86, 2005, pp. 1097-1107.

H. Noureddini and D. Zhu, University of Nebraska, "Kinetics of Transesterification of Soybean Oil", JAOCS, vol. 74, No. 11, 1997, pp. 1457-1463.

Ulf Schuchardt et al., "Transesterification of Vegetable Oils: a Review", J. Braz. Chem. Soc., vol. 9, No. 1, 1998, pp. 199-210.

Gerhard Knothe et al., "Biodiesel: The Use of Vegetable Oils and Their Derivatives as Alternative Diesel Fuels", U.S. Department of Agriculture, Peoria, IL, ACS Symp. Ser., 1997, 666, pp. 172-208.

Ahmad A. Al-Dhubabian, "Production of Biodiesel from Soybean Oil in a Micro Scale Reactor", Thesis for the degree of Master of Science in Chemical Engineering, Oregon State University, Mar. 16, 2005, 145 pages.

* cited by examiner

METHODS AND SYSTEMS FOR IMPROVED BIODIESEL PRODUCTION

BACKGROUND

The present disclosure relates generally to the transesterification of oils and fats in the presence of a catalyst to produce biodiesel.

Fatty acids of alkyl esters are commonly known as biodiesel. A biodiesel may be described as a mixture of mono alkyl esters (e.g., methyl esters) derived from renewable sources such as biolipids that may include vegetable oils and animal fats. Biodiesel is technically acceptable as a direct replacement or blending stock for petroleum diesel. Thus, biodiesel is a beneficial alternative fuel source due to its biodegradability, non-toxicity, and low emission profiles compared to conventional fuel sources. Biodiesel may be produced by a catalytic transesterification process that facilitates an organic chemical reaction between biolipids (e.g., animal fat and vegetable oil) and alcohol in the presence of a catalyst to form the mixture of mono alkyl esters and glycerol.

Traditional methods and systems for producing biodiesel may be limited since the transesterification reaction is mass transfer limited due to the properties of the reactants. Mechanical agitation and heat application techniques are being used to improve the mass and heat transfer characteristics of the transesterification process. However, these techniques produce emulsions that increase the settling time, increase the energy required for product separation, and increase the scale of the process equipment. Therefore, there is a need for an improved catalytic transesterification process.

SUMMARY

Deployment of known techniques to improve the mass and heat transfer characteristics of the transesterification reaction may not provide a biodiesel production process that has desirable features such as high volume, low capital and operating costs, short residence times (a residence time may be indicative of an average time required for a material to be transferred between two reference points), compact and modular process equipment design, moderate process conditions, and low energy usage. The foregoing needs are addressed by the teachings of the present disclosure, which relates to methods and systems for improved biodiesel production. According to some embodiments, a method and system to produce biodiesel using an improved catalytic transesterification process, includes a first reactant and a second reactant that are dispersed to form a laminar slug flow pattern within a microchannel of a microreactor, the first reactant and the second reactant being immiscible. The first reactant and the second reactant are mixed, thereby triggering a reaction between them to produce the biodiesel and glycerol, the mixing being convection-enhanced by shear stress induced circulation occurring within each slug of the reactants. The reaction takes place under a pressure that is less than 5 psi and under a temperature that is less than 70 degrees Celsius. Separation of the glycerol from the biodiesel occurs simultaneously with the mixing. Several microreactors are coupled in parallel to improve throughput of the biodiesel.

Several advantages are achieved by the method and system according to the illustrative embodiments presented herein. The embodiments advantageously provide an improved catalytic transesterification process by using a turbulence free segmented flow pattern having features such as high volume biodiesel production by using a stacked arrangement of modules, low capital and operating costs, low residence times by using a continuous microreactor, a compact and modular process equipment design that enables operation in remote areas, farms, and developing countries, low to moderate operating conditions for the process, and low energy usage.

DETAILED DESCRIPTION

Figure 1A:
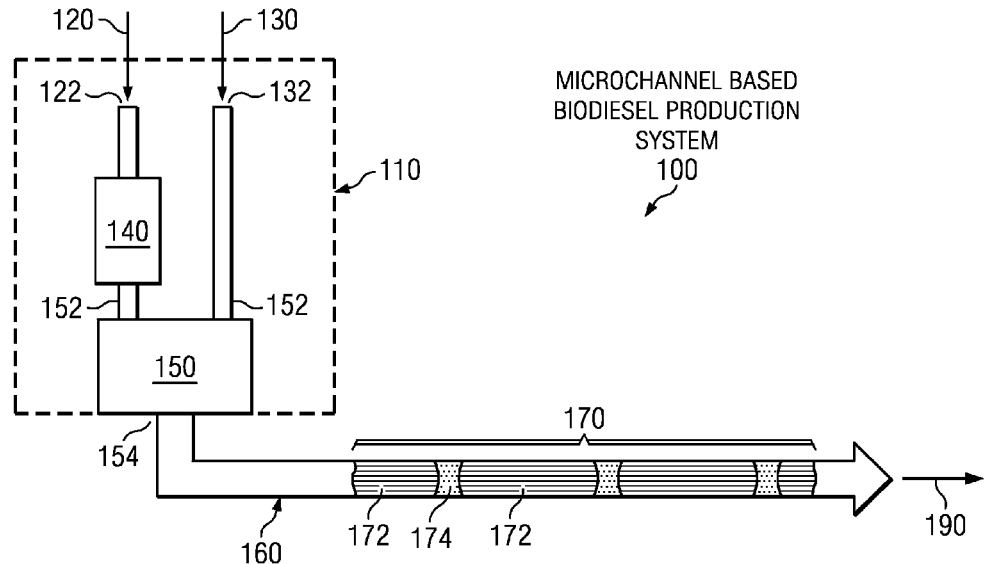
FIG. 1A illustrates a microchannel based biodiesel production system, according to some embodiments.

Novel features believed characteristic of the present disclosure are set forth in the appended claims. The disclosure itself, however, as well as a preferred mode of use, various objectives and advantages thereof, will best be understood by reference to the following detailed description of illustrative embodiments when read in conjunction with the accompanying drawings. The functionality of various mechanical elements, members, or components for forming modules, sub-assemblies and assemblies assembled in accordance with a structure for an apparatus may be implemented using various materials and coupling techniques, depending on the application requirements. Descriptive and directional terms used in the written description such as top, bottom, left, right, and similar others, refer to the drawings themselves as laid out on the paper and not to physical limitations of the disclosure unless specifically noted. The accompanying drawings may not to be drawn to scale and some features of embodiments shown and described herein may be simplified or exaggerated for illustrating the principles, features, and advantages of the disclosure.

Applicants recognize that present mesoscale approaches of producing biodiesel generally involve the mixing of immiscible reactants (oil and alcohol) with continuous mechanical stirring (batch) or turbulent static mixers (continuous). Both approaches typically result in a dispersion of small droplets of one phase in the other. Though this approach enhances mixing of the reactants, separation of the products typically requires long settling times (e.g., 8 hours or more) or requires a centrifuging stage for the separation. In addition, the slow separation of the products provides the opportunity for a reverse reaction to occur, which will ultimately reduce yields unless the residence time is made sufficiently long (usually 2-3 hours).

Therefore, a need exists to provide improved mass and heat transfer characteristics of the transesterification reaction. This problem may be addressed by an improved catalytic transesterification process that has desirable features such as high volume, low capital and operating costs, low residence times, compact and modular process equipment design, moderate process conditions, and low energy usage.

According to some embodiments, a method and system to produce biodiesel using an improved catalytic transesterification process, includes a first reactant and a second reactant that are dispersed to form a laminar slug flow pattern within a microchannel of a microreactor, the first reactant and the second reactant being immiscible. The first reactant and the second reactant are mixed, thereby triggering a reaction between them to produce the biodiesel and glycerol, the mixing being convection-enhanced by shear stress induced circulation occurring within each slug of the reactants. The reaction takes place under a pressure that is less than 5 psi and under a temperature that is less than 70 degrees Celsius. Separation of the glycerol from the biodiesel occurs simultaneously with the mixing. Several microreactors are coupled in parallel to improve throughput of the biodiesel.

The following terminology may be useful in understanding the present disclosure. It is to be understood that the terminology described herein is for the purpose of description and should not be regarded as limiting.

Mechanical connection and coupling—The term 'connection or connected' refers to a direct mechanical connection between the devices or components that are connected, without the presence of any intermediate device(s) or component(s). The term 'coupling or coupled' refers to either a direct mechanical connection between the devices or components that are connected or an indirect connection through one or more intermediary device(s) or component(s). The devices or components may be passive or active.

Configuration—Describes a set up of an element, a device, a reactant, a catalyst, and similar other, and refers to a process for setting, defining, or selecting particular properties, parameters, or attributes of the element prior to its use or during its operation. Some configuration attributes may be selected to have a default value. For example, process equipment used in a transesterification process may be configured to operate under low pressure (e.g., less than 5 psi) and moderate temperature (e.g., less than 70 degrees Celsius) conditions.

System—Interdependent devices or components that cooperate to perform one or more desired functions.

Embodiments of improved microscale biodiesel production systems and methods are described with reference to FIGS. 1A-1C, 2A-2G, 3A-3D, 4A, 4B, and 5.

FIG. 1A illustrates a microchannel based biodiesel production system 100, according to some embodiments. The system 100 includes an intake assembly 110 to receive a first reactant 120 via a first inlet 122 and a second reactant 130 via a second inlet 132. The intake assembly 110 also includes a passive flow dispenser 140 coupled to an adder 150. The passive flow dispenser 140 that is coupled to receive the first reactant 120 from the first inlet 122 is operable to control a flow rate of the first reactant 120. In the depicted embodiments, the adder 150, which may be in the shape of a Y tube, includes two adder inlets 152 and an adder outlet 154.

The choice of input raw materials and catalysts used in the transesterification process may be dependent on the biodiesel application requirements. That is, the availability of biolipid sources may place additional constraints on the biodiesel production process. In some embodiments, the first reactant 120 may be a biolipid and the second reactant 130 may include a mixture of alcohol (e.g., methanol or ethanol) and a catalyst. In some embodiments, the catalyst may be selectable to be one of an acid and a base chemical. In some embodiments, the first reactant 120 and the second reactant 130 are immiscible.

The adder outlet 154 is coupled to a microchannel 160 having a configurable geometry. The microchannel 160 acts as a continuous plug flow reactor for the transesterification process. That is, the first reactant 120 and the second reactant 130 react within the microchannel 160 to produce the biodiesel 190 and glycerol as outputs. Configuration of the microchannel 160 may affect the biodiesel production performance including throughput (rate and quantity), residence time, and others. For example, in one biodiesel production application, dimensions such as the diameter of the microchannel 160 may be configured to be between 300 micrometers and 700 micrometers to achieve a desired production rate. As another example, another microchannel may have a square cross section having a side equal to about 300 micrometers to about 700 micrometers for the desired residence time.

The two adder inlets 152 are respectively coupled to the passive flow dispenser 140 and the second inlet 132. The adder 150 working in combination with the passive flow dispenser 140 is operable to dispense the first reactant 120 and the second reactant 130 to form a laminar slug flow pattern 170 (although the microchannel 160 may be opaque, for clarity the laminar slug flow pattern 170 is illustrated in a transparent portion of the microchannel 160; the pattern 170 may also be referred to as a segmented laminar flow pattern 170) within the microchannel 160. The laminar slug flow pattern 170 comprises the formation of alternate slugs 172 and 174 of the first reactant 120 and the second reactant 130, respectively, within the microchannel 160. As seen in FIG. 1A, slugs 172 and 174 alternate in the direction of flow through microchannel 160. Slug 172 may be referred to as a first slug, and slug 174 may be referred to as a second slug. The flow of the first reactant 120 and the second reactant 130 in the form the laminar slug flow pattern 170 is laminar (or turbulence free). That is, the Reynolds number for the flow is far less than 1.

In some embodiments, the passive flow dispenser 140 and the adder 150 may be used to control a proportion (or ratio) of the first reactant 120 relative to the second reactant 130. For example, in some embodiments, a molar ratio between the first reactant 120 and the second reactant 130 may be configured to be equal to 1:7.2 to optimize the transesterification process.

Figure 1C:
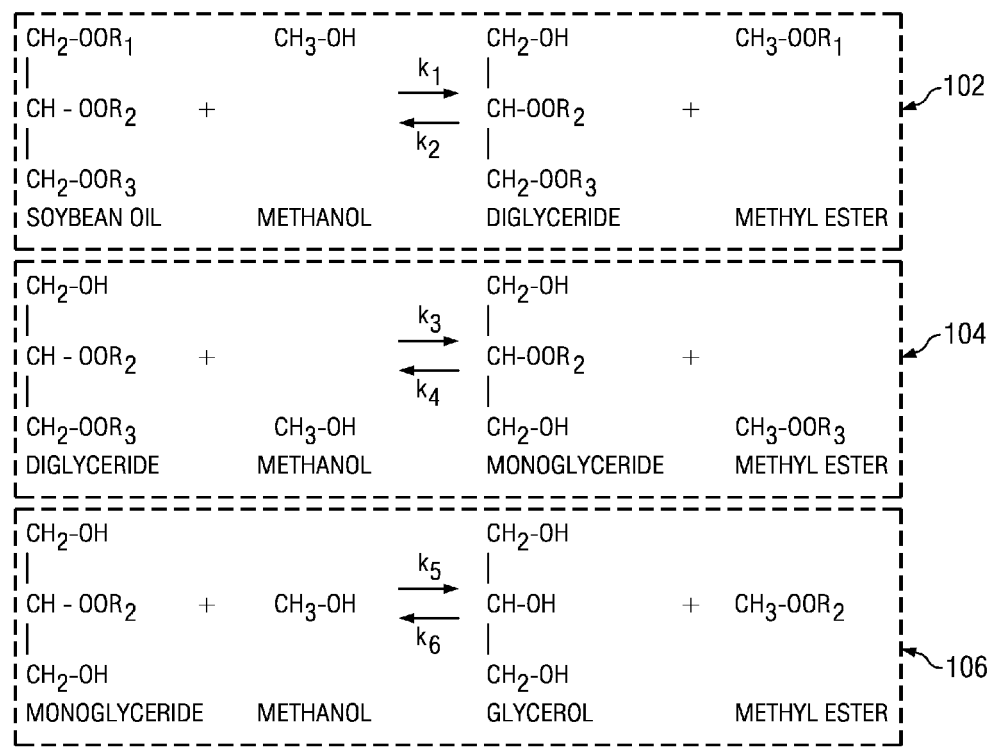
FIG. 1C illustrates details of a multi-step catalytic transesterification process described with reference to FIGS. 1A and 1B, according to some embodiments.
Figure 1B:
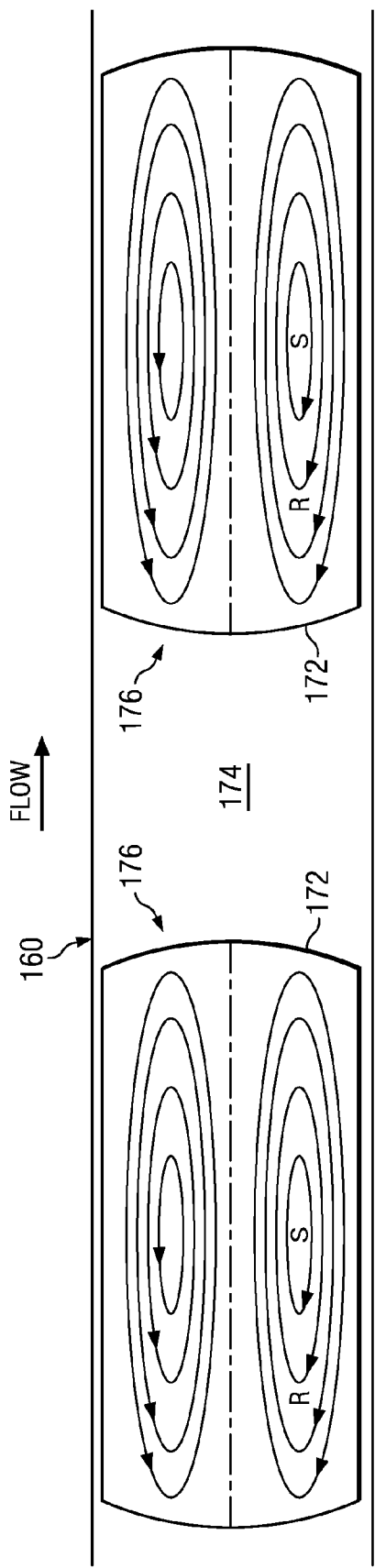
FIG. 1B illustrates convection-enhanced mixing within a microchannel described with reference to FIG. 1A, according to some embodiments.

FIG. 1B illustrates convection-enhanced mixing within a microchannel described with reference to FIG. 1A, according to some embodiments. The laminar slug flow approach deployed within the microchannel 160 is a microscale flow pattern that creates an internal convection-enhanced mixing current which improves the mass transfer considerably compared to the traditional diffusion-only mixing. The mixing of the two reactants 120 and 130 occurs by diffusion across an interface 176. The internal convection-enhanced mixing current (e.g., induced by a vortex) simply moves the reactants from the middle of the segment to the interface 176 where it then interacts with the other reactants. The vortex itself may not mix the two reactants 120 and 130; it may simply move molecules that are far away closer to the interface 176. Without the formation of the vortices that facilitate internal convection-enhanced mixing, the molecules in the center of the segment or slug (e.g., stagnant molecules) have to undergo diffusion (a slow moving process) to reach the interface 176. Adding the vortex feature to the flow dramatically speeds this motion, thereby enhancing the catalytic transesterification process. As described earlier, the mixing of the first reactant 120 and the second reactant 130 triggers a reaction that produces the biodiesel 190 and glycerol. The mixing is convection-enhanced by shear stress induced circulation (in the form of vortices in the clockwise and counterclockwise directions) occurring within each slug 172 and 174 of the reactants 120 and 130 respectively. Although, FIG. 1B shows vortices formed in the clockwise and counterclockwise directions within the slug 172, it is understood that similar vortices are also formed in the slug 174. Vortices formed in the slug 174 are not shown for simplification and clarity purpose. An amount of the induced shear stress may be controlled by configuring the geometry and material properties of the microchannel 160. The segmented pattern increases the active interface 176 between the slugs 172 and 174, respectively, formed by the first reactant 120 and the second reactant 130, leading to improved mass transfer. With this pattern, a significant mass transfer may be achieved at relatively large microchannel diameters (e.g., 300 to 700 micrometers). This has the effect of reducing the residence time for conversion of the biolipid and alcohol to biodiesel and glycerol. For example, in one application, the residence time for biodiesel is less than four minutes with the microchannel diameter being configured to be equal to 500 micrometers.

In addition, the laminar slug flow pattern 170 provides automatic separation of the glycerol and the biodiesel 190 phases by avoiding the generation of a microemulsion that occurs with turbulent mixing. Thus, the mixing and separation operations occur simultaneously by deploying a laminar, turbulent-free segmented pattern within the microchannel 160. This nearly instant separation of the biodiesel 190 and the glycerol allows for the construction of continuous multi-stage reactors described in further detail with reference to FIG. 3A-3D. The separation also reduces the possibility of a reverse reaction (described with reference to FIG. 1C) from occurring.

The improved catalytic transesterification process described with reference to FIGS. 1A and 1B is configurable to operate under lower pressure and lower temperature compared to traditional processes. In an exemplary, non-depicted embodiment, a water bath with an immersion heater and a thermostat may be used for maintaining the temperature at a desired set point. An electric pipe heater with an adjustable power supply may also be used. In some embodiments deploying the water bath, the reactor may be submerged in the heated water to give isothermal conditions. In some embodiments deploying the pipe heater, the oil may be heated continuously as it flows through the reactor modules. In addition, a pipe heater or heat exchanger may be deployed to heat the reactants 120 and 130 before entering the reactor. The temperature going in and out of the reactor module may be monitored with thermocouples, that may be imbedded in the tubes. In some embodiments, the mixing and the separation processes taking place within the microchannel 160 operate under a pressure that is less than 5 psi and a temperature that is less than 70 degrees Celsius. Additional details of a benchmark comparison between the improved catalytic transesterification process and a traditional batch reactor based process is described with reference to FIG. 5.

FIG. 1C illustrates details of a multi-step catalytic transesterification process described with reference to FIGS. 1A and 1B, according to some embodiments. In the depicted embodiment, the first reactant 120 is a triglyceride and the second reactant 130 is methanol mixed with a catalyst. The multi-step catalytic transesterification process includes three (3) reversible reactions 102, 104, and 106 in the presence of the catalyst to produce the biodiesel 190 and glycerol. The biodiesel and glycerol produced are immiscible fluids. Under ideal process conditions, the glycerol is pulled into the methanol phase as it is produced. However, since the reaction does not take place exclusively at the interface 176, there may be some time required for the glycerol to travel to the methanol. The vortices inside the slugs greatly reduces this time, thereby limiting the amount of reverse reactions. Since the solubility of methanol in the oil phase increases as the ester concentration grows, the volume of the methanol slug may be reduced slightly.

Figure 2C:
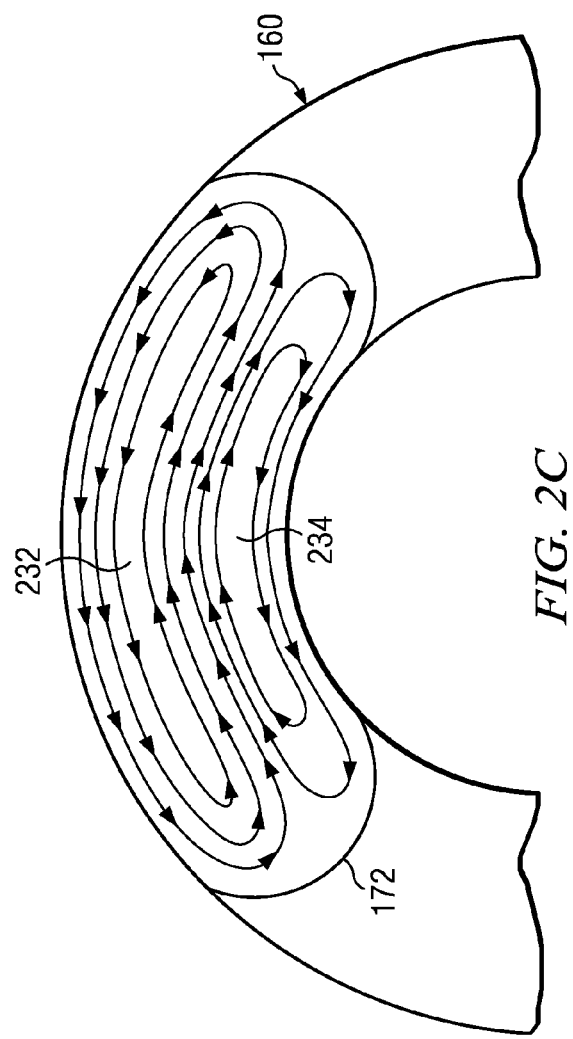
FIG. 2C illustrates additional details of a fluid flow through a microchannel described with reference to FIGS. 1A, 1B, 2A and 2B according to some embodiments.
Figure 2A:
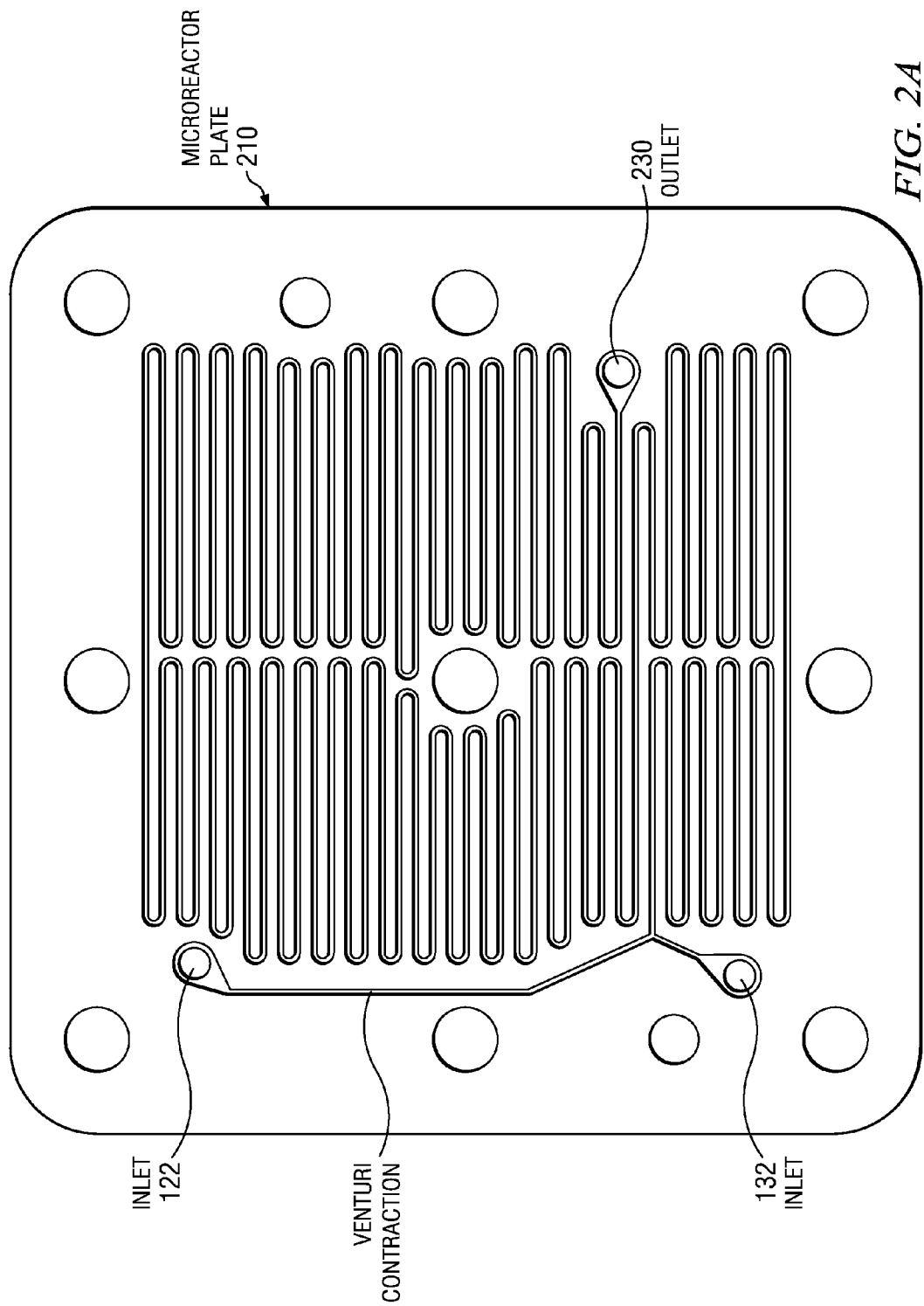
FIG. 2A illustrates a microreactor plate, according to some embodiments.
Figure 2B:
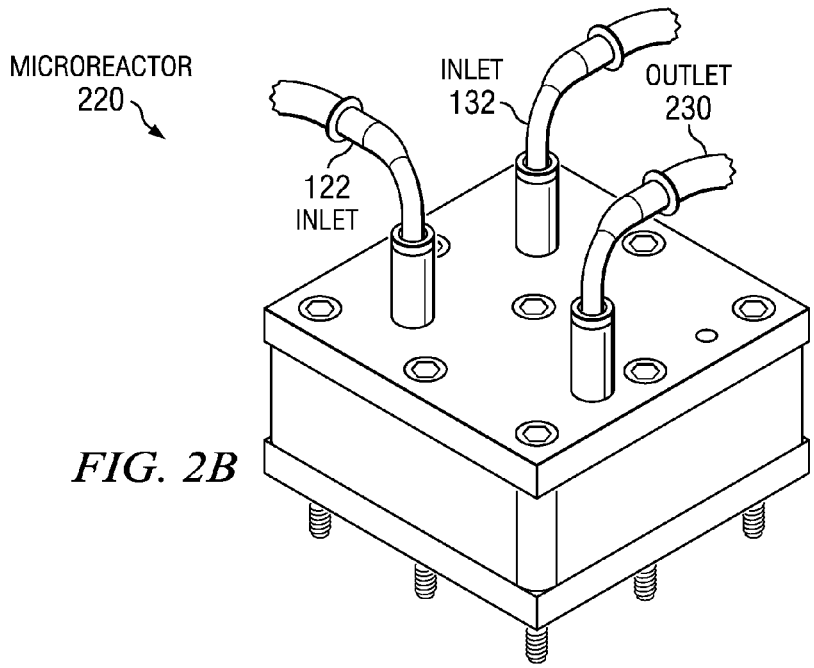
FIG. 2B illustrates a microreactor, according to some embodiments.

FIG. 2A illustrates a microreactor plate 210, according to some embodiments. The microreactor plate 210 comprises one or more microchannels (described with reference to FIGS. 1A and 1B) coupled in parallel for improved throughput. FIG. 2B illustrates a microreactor module 220, according to some embodiments. The microreactor module 220 comprises one or more of the microreactor plate 210 (described with reference to FIG. 2A) coupled in a stacked arrangement for improved throughput.

Referring to FIGS. 2A and 2B, the microreactor module 220 includes at least one of the microreactor plate 210, the intake assembly 110 (for receiving the reactants 120, 130) described with reference to FIGS. 1A and 1B, and an outlet 230 to provide the biodiesel 190 produced by each one of the microchannel 160 of the microreactor plate 210.

In some embodiments, the microreactor plate 210 is composed of one or more ones of the microchannel 160 (also referred as reaction channels) having a length L and a cross section having a configurable shape. In some embodiments, the cross-section dimensions may be configured to be equal to 500 um×500 um. The reactants, e.g., methanol and oil, are fed through separate inlets that come together at a Y-shaped adder that generates the segmented flow pattern. The methanol inlet is connected to a Venturi Contraction (250 um×250 um) that provides passive volume flow control. The microreactor plate 210 may be contracted in an inert polymer (e.g., high-density polyethylene (HDPE)) by hot embossing with a press. The HDPE microreactor plates may be sealed with another thin layer of HDPE by hot lamination, also with a press. The individual microreactor plates may then be stacked into one or more modules. Each microreactor module 220 may include N individual microreactor plates, where N may be configured to be selectable between 5 and 100. Thus, each microreactor module 220 may be capable of producing N times the volume flow rate of a single microreactor plate. The microreactor module 220 may also include an end plate having multiple openings. Some of the openings may be configured for transferring fluids to/from the microreactor module 220 and some of the openings may be configured for accommodating alignment and support members.

Each one of the microchannel 160 included in the microreactor plate 210 may be configured to have an optimal length L to optimize residence time, desired pressure at the inlet and outlet, and complexity of the manifold design. If one desires to maintain a desired residence time, a longer length may give a higher slug speed and greater mass transfer by convection within the slug. However, it may also create a higher pressure drop. It may be desirable to maintain reasonable pressure heads (e.g., less than 20 psi at inlet). If the length of the microchannel 160 is too short, the slug may move too slowly for the convection process to be effective. In addition, to achieve a fixed residence time, a shorter length L of the microchannel 160 may give a lower mean velocity and lower flow rate. Therefore, an additional number of microchannels may be desirable to be coupled in parallel to get higher flow rates. Additional details of a manifold design to couple microchannels in parallel are described with reference to FIGS. 2D and 2G. By using a longer length L of the microchannel 160, one may obtain higher mean velocities (for a fixed residence time) and a higher flow rate and, therefore, a fewer number of microchannels may be needed. In some embodiments, the length L for a microchannel is configured to be equal to about 60 inches to achieve a compromise between a higher pressure head and less complexity of the manifold design.

FIG. 2C illustrates additional details of a fluid flow through a microchannel described with reference to FIGS. 1A, 1B, 2A and 2B according to some embodiments. In the depicted embodiment, the reactants 120 and 130 flow in one direction since there is only one outlet 230. The venturi contraction provides resistance to the oil flow so that it may not provide an outlet through the methanol inlet, and hence it travels along a length L of the microchannel to the outlet 230. In some embodiments, the length L may be configured to be equal to five feet. The path traversed by the reactants 120 and 130 may be narrow and may include multiple bends (e.g., U-turns). The bends serve to perturb the fluid in the center of the vortices. When the fluid segment travels around a bend, one side moves faster than the other due to longer path length of the wall (e.g., the outside wall) of the bend. The phenomenon is analogous to an automobile maneuvering a road bend. That is, when the automobile turns through the road bend, the wheels disposed on the outer side of the bend move faster relative to the wheels disposed on the inner side of the bend. The conservation of mass law causes an increase in the speed of the outer side of the segment relative to the inner side, thereby causing an outer vortex 232 to spin faster than an inner vortex 234 and become larger (the vortices 232 and 234 are spinning in opposing directions). This shifts the center of the vortex, and at the same time, causes the molecules near the center of the vortex to move to other faster moving layers. The center of the vortex is nearly stagnant, so the technique of causing the microchannel (and hence the fluid) to turn or bend frequently promotes the movement of the stagnant fluid so that it travels to the interface where it can react.

Figure 2D:
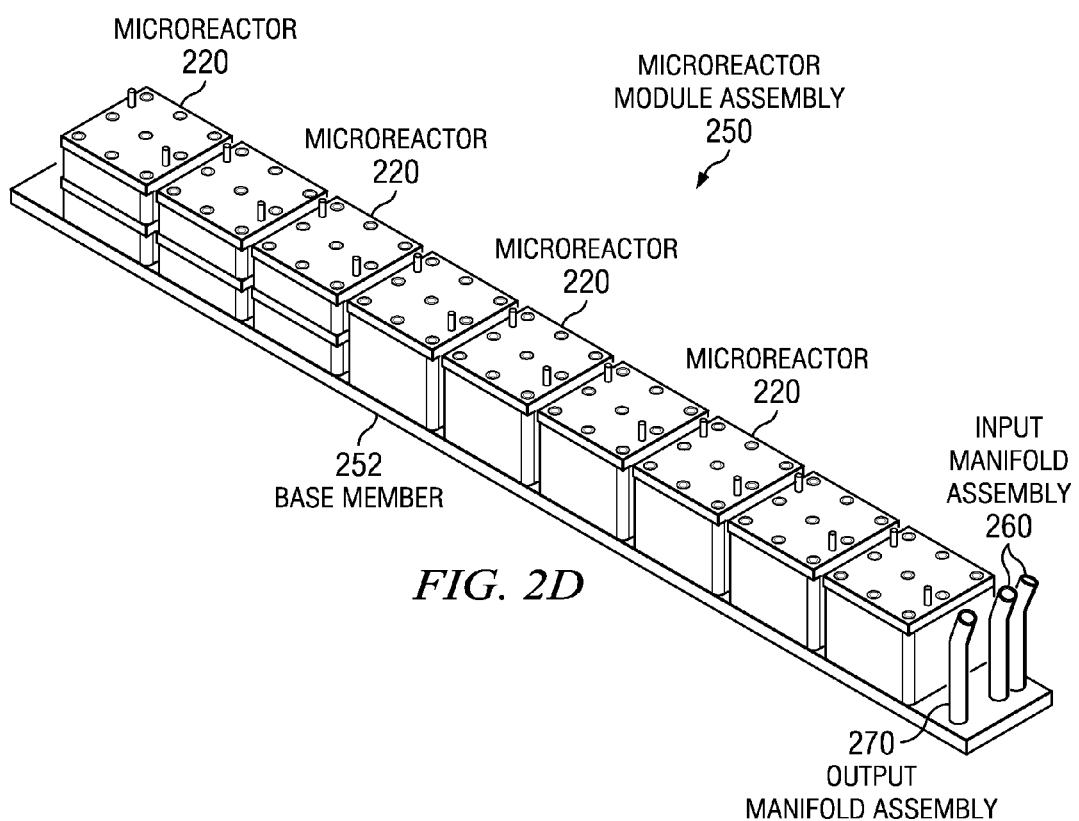
FIG. 2D illustrates a microreactor module assembly, according to some embodiments.

FIG. 2D illustrates a microreactor module assembly 250, according to some embodiments. The features and operation of the microreactor module assembly 250 is substantially the same as those of the microreactor module 220 described with reference to FIG. 2B except for the biodiesel throughput. The microreactor modular assembly 250 comprises one or more of the microreactor modules 220 (described with reference to FIG. 2B) disposed adjacent to one another for improved throughput. In the depicted embodiment, N ones (where N=9) of the microreactor module 220 are arranged in parallel and connected by an input manifold assembly 260 to receive the first reactant 120 and the second reactant 130 and an output manifold assembly 270 to receive the biodiesel 190 produced by each one of the microchannel 160, thereby creating a high-volume flow rate (e.g., up to 0.5 million gallons per year). A base member 252 of the microreactor module assembly 250 may be configured to provide structural support and accommodate piping to transfer fluids to/from the manifold assemblies 260 and 270 to each one of the microreactor 220. To achieve a desired biodiesel production rate of about 0.5 million gallons/year, it is estimated that approximately N=10, 000 microreactor plates may be needed to be coupled in parallel.

Figure 2E:
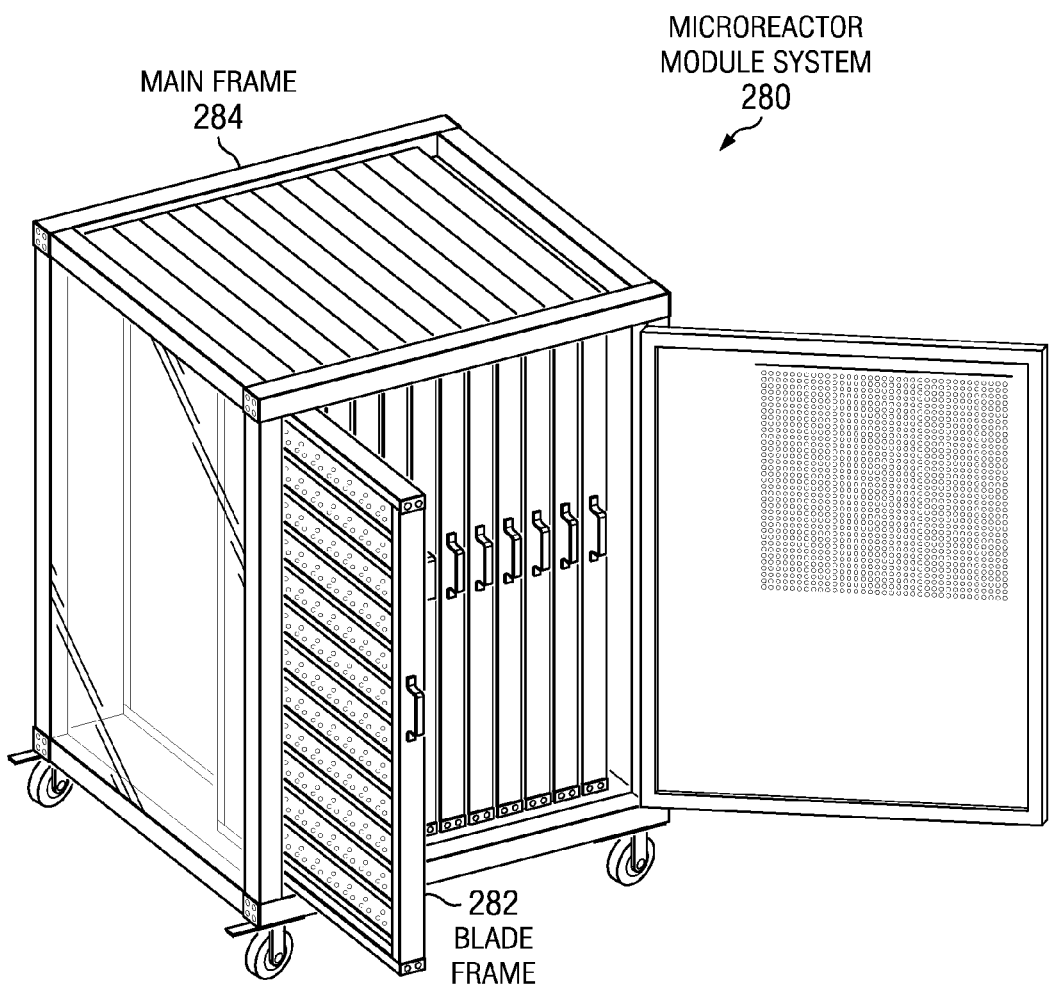
FIG. 2E illustrates a microreactor modular system, according to some embodiments.
Figure 2F:
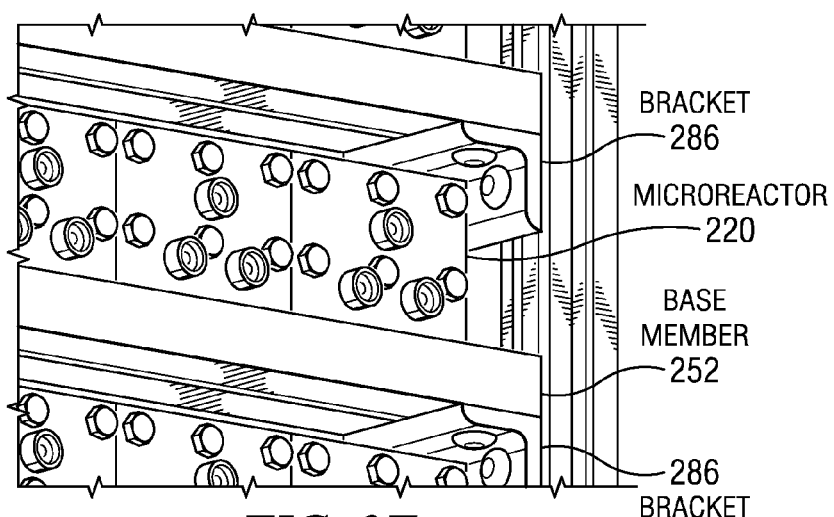
FIG. 2F illustrates additional details of a blade frame described with reference to FIG. 2E, according to some embodiments.
Figure 2G:
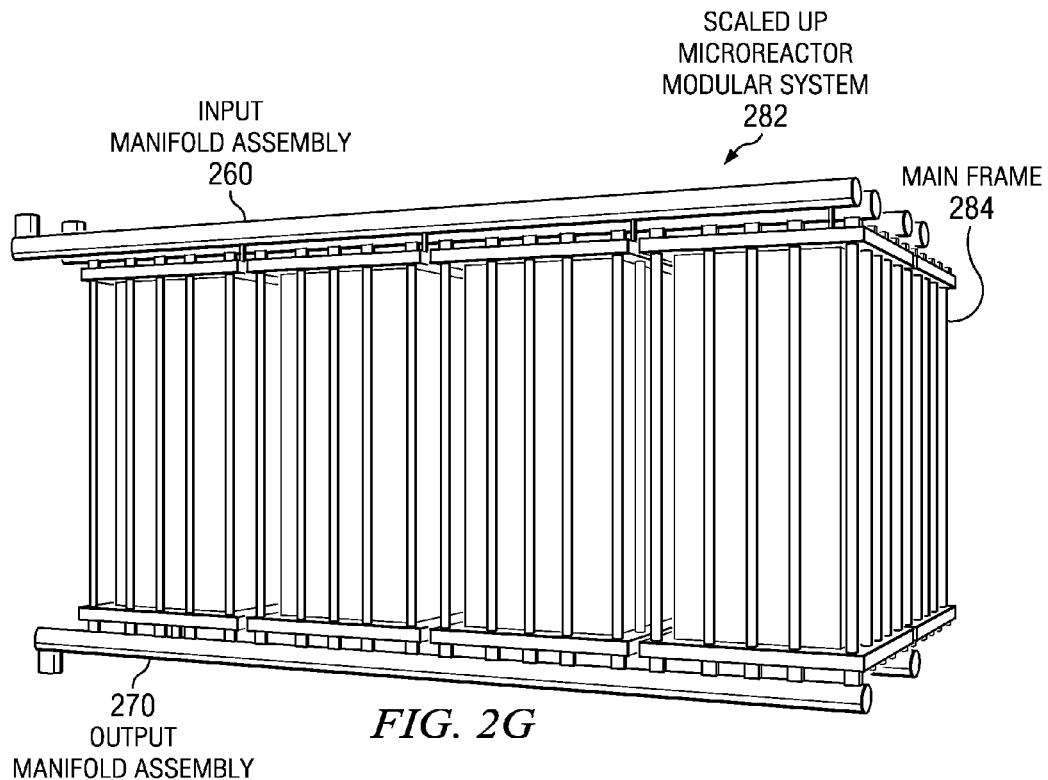
FIG. 2G illustrates another configuration of a microreactor modular system described with reference to FIG. 2E, according to some embodiments.

FIG. 2E illustrates an isometric view of a microreactor modular system 280, according to some embodiments. FIG. 2F illustrates additional details of a blade frame 282 described with reference to FIG. 2E, according to some embodiments. FIG. 2G illustrates a scaled up microreactor modular system 282, according to some embodiments. Referring to FIGS. 2E, 2F and 2G, the features and operation of the microreactor modular system 280 and 282 is substantially the same as those of the microreactor module assembly 250 described with reference to FIG. 2D except for the biodiesel throughput. The microreactor modular system 280 comprises one or more of the microreactor module assembly 250 (described with reference to FIG. 2D) coupled in a stacked arrangement on a blade frame 282, and multiple ones of the blade frame 282 being housed within a mainframe 284 for improved throughput. The blade frame 282 may be configured to slide in and out of corresponding slots of the mainframe 284 for performing functions such as servicing, maintenance, inspection, repair, and others. The base member 252 of each microreactor module assembly 250 included in the microreactor blade frame 282 may be supported by a pair of angle bars or brackets 286. The dimensions of the blade frame 282 and the mainframe 284 may be configured to facilitate maintainability, flexibility, modular growth, and ease of assembly. It may be desirable that no special tools may be required to assemble this structure. Flexible tubing (not shown) that facilitates unobstructed sliding in/out of the blade frame 282 may be used to couple the fluid transfer to/from the one or more of the microreactor module assembly 250. In an exemplary, non-depicted embodiment, the mainframe 284 may also include other components, including a separator, flow meter, heat exchanger, the manifold assemblies 260, 270 and others. Referring to FIG. 2G, the scaled up microreactor modular system 282 included additional ones of the microreactor modular system 280. That is, the system 280 being modular may be easily scaled up by coupling the manifold assemblies 260 and 270 to additional ones of the mainframe 284 connected in parallel to accommodate various desired production rates up to 1 million gallons per year.

Figure 3A:
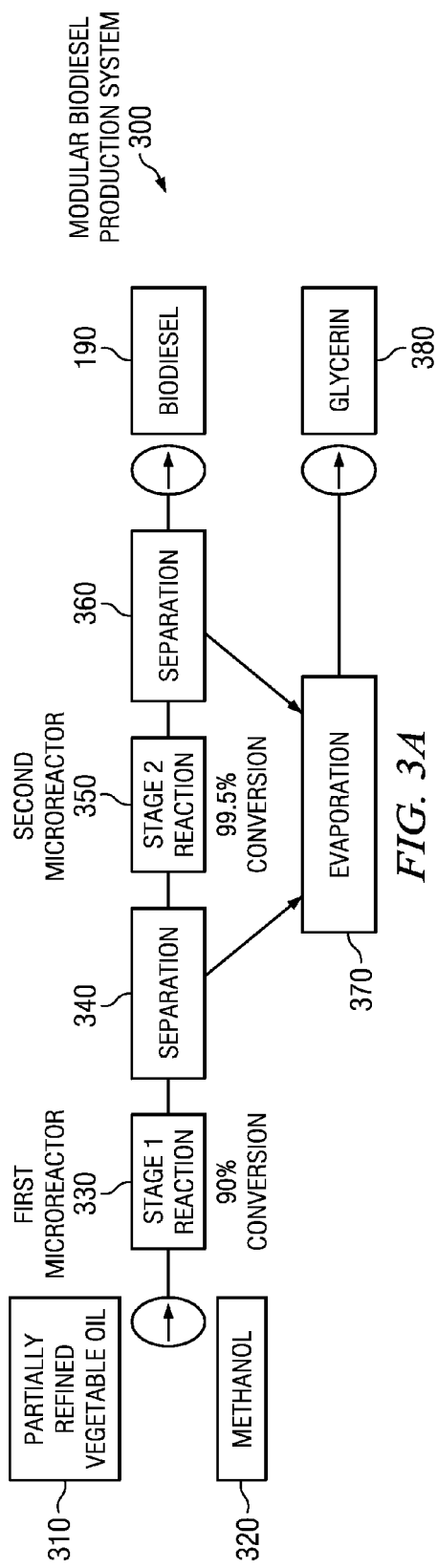
FIG. 3A illustrates a modular biodiesel production system using a 2-stage conversion process, according to some embodiments.
Figure 3B:
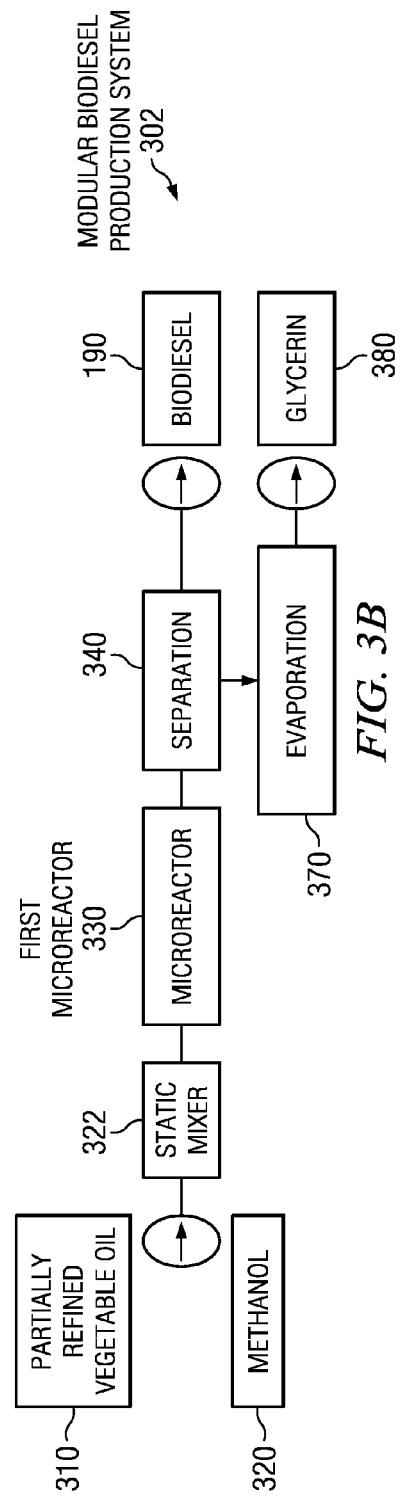
FIG. 3B illustrates a modular biodiesel production system using a 1-stage conversion process with a static mixer, according to some embodiments.
Figure 3C:
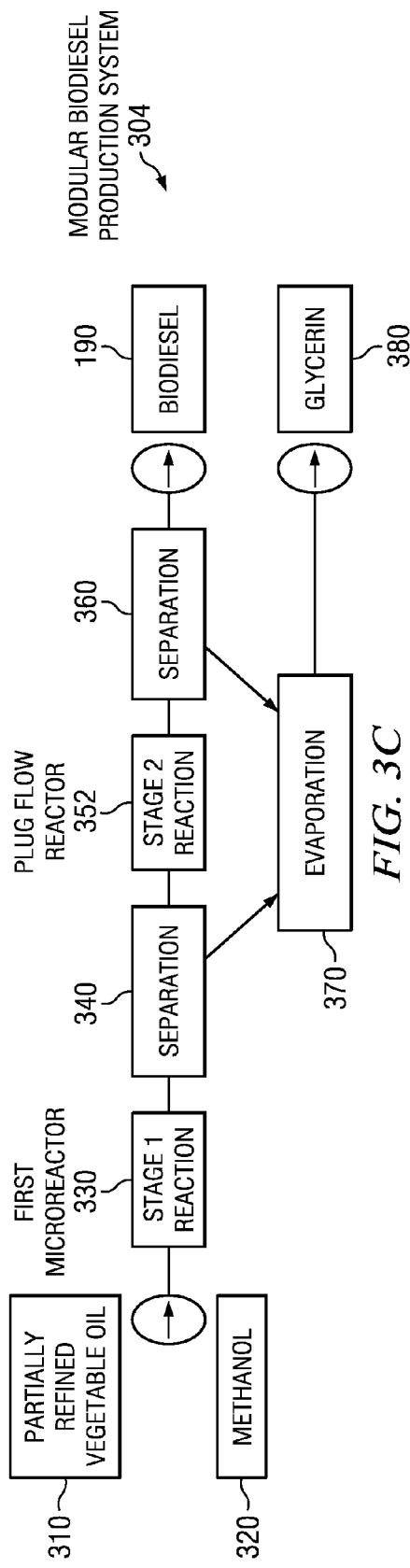
FIG. 3C illustrates a modular biodiesel production system using a 2-stage conversion process with a plug flow reactor, according to some embodiments.
Figure 3D:
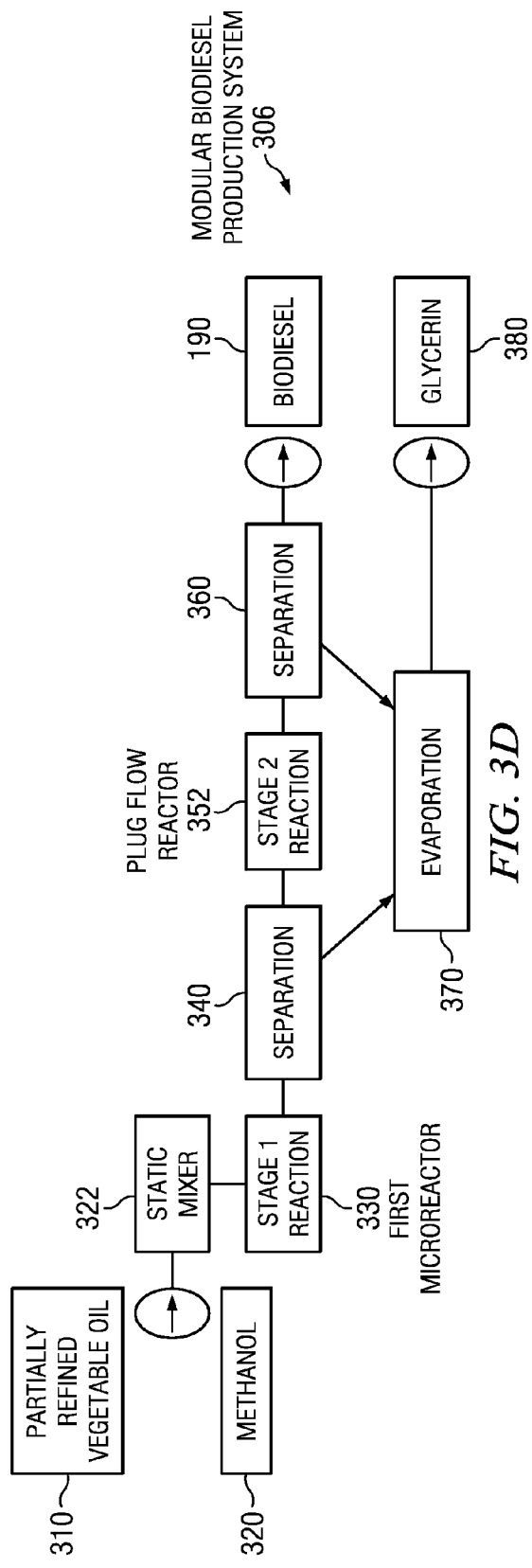
FIG. 3D illustrates a modular biodiesel production system using a 2-stage conversion process with a plug flow reactor and a static mixer, according to some embodiments.

FIG. 3A illustrates a modular biodiesel production system 300 using a 2-stage conversion process, according to some embodiments. FIG. 3B illustrates a modular biodiesel production system 302 using a 1-stage conversion process with a static mixer, according to some embodiments. FIG. 3C illustrates a modular biodiesel production system 304 using a 2-stage conversion process with a plug flow reactor (PFR), according to some embodiments. FIG. 3D illustrates a modular biodiesel production system 306 using a 2-stage conversion with a plug flow reactor and a static mixer, according to some embodiments. Referring to FIGS. 3A, 3B, 3C, and 3D, the modular biodiesel production system 300, 302, 304, and 306 may include one or more ones of the microreactor module 220, the microreactor module assembly 250, the microreactor modular system 280 and 282 or a combination thereof described with reference to FIGS. 2A-2G. In some embodiments, a first source 310 is operable to provide the first reactant 120 and a second source 320 is operable to provide the second reactant 130. A first microreactor 330 (which may be the same as the microreactor 220, the microreactor module assembly 250, or a combination thereof) is coupled to the first source 310 and the second source 320 is operable to produce the biodiesel 190. Although the first microreactor 330 automatically performs the separation along with the mixing, the modular biodiesel production system 300, 302, 304, 306 may include a first separator 340 to further separate the biodiesel 190 and the glycerol received from the first microreactor 330. In some embodiments, a static mixer 322 may be included before the first microreactor 330 to receive the reactants 120 and 130, mix them, and provide it to the first microreactor 330. As described herein, a static mixer may be any device that may include one or more non-moving elements for mixing or blending two fluid materials. In some embodiments, the static mixer 322 may be configured to achieve 70-80% conversion efficiency compared to 90% efficiency for a single-stage microreactor.

Since a single-stage microreactor based process may achieve a 90% conversion efficiency, it may be desirable to recover additional biodiesel by adding second-stage processing to a single-stage based system, such as the modular biodiesel production system 302. A second microreactor 350 may be coupled to receive the unused portion of the first reactant 120 and the second reactant 130 from the first microreactor 330, the unused (or unreacted) portion of the first reactant 120 and the second reactant 130 being mixed to produce additional biodiesel. In some embodiments, a plug flow reactor (PFR) 352 may be used in place of the second microreactor 350. As described herein, the PFR 352 may be configured as a well known type of a chemical reactor in the form of a pipe or a tube. Chemical reaction typically occurs as the reactants travel through the PFR 352. In an exemplary, non-depicted embodiment, the second microreactor 350 may be coupled to receive the new supply of the first reactant 120 and the second reactant 130 that may be added to the unused portion. It is estimated that a two-stage microreactor production process may achieve a 99.5% conversion efficiency. Although the second microreactor 350 automatically performs the separation along with the mixing, the modular biodiesel production system 300 may include a second separator 360 to further separate the biodiesel 190 and the glycerol received from the second microreactor 350. The two separators 340 and 360 may be input to an evaporator 370 to recover the glycerin 380.

In some embodiments, the separators 340 and 360 may use gravity to separate the biodiesel and glycerol. In the multi-step catalytic transesterification process described with reference to FIG. 1C, the glycerol is pulled from the ester phase into the methanol phase (both are alcohols, they are both very hydrophilic) as it is produced. The contact between the glycerol and the esters is limited to the interface only, which is a relatively small surface area. The glycerol may not diffuse into the ester phase since it prefers to stay with the methanol. The methanol and catalyst also react at the interface at first, but at a certain point, they may start diffusing into the oil/ester phase and react in the volume of the segment itself. This may happen rapidly when the ester content becomes significant (50%), since the solubility of the methanol and the catalyst may be improving in the oil phase as the ester concentration increases.

Figure 4A:
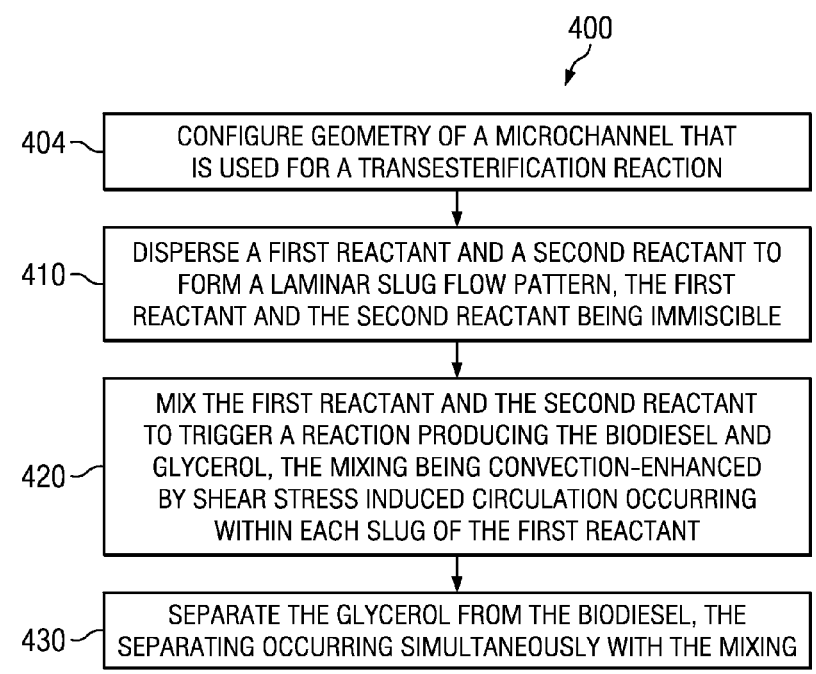
FIG. 4A illustrates a flowchart of a method for producing biodiesel, according to some embodiments.

FIG. 4A illustrates a flowchart of a method 400 for producing biodiesel, according to some embodiments. In some embodiments, the method 400 is used for producing biodiesel by deploying biodiesel production systems described with reference to FIGS. 1A-1C, 2A-2G, and 3A-3D. Referring to FIG. 4A, at process 410, a first reactant and a second reactant are dispersed to form a laminar slug flow pattern, the first reactant and the second reactant being immiscible. At process 420, the first reactant and the second reactant are mixed to trigger a reaction producing the biodiesel and glycerol, the mixing being convection-enhanced by shear stress induced circulation occurring within each slug of the reactants. At process 430, the glycerol is separated from the biodiesel, the separating occurring simultaneously with the mixing.

Figure 4B:
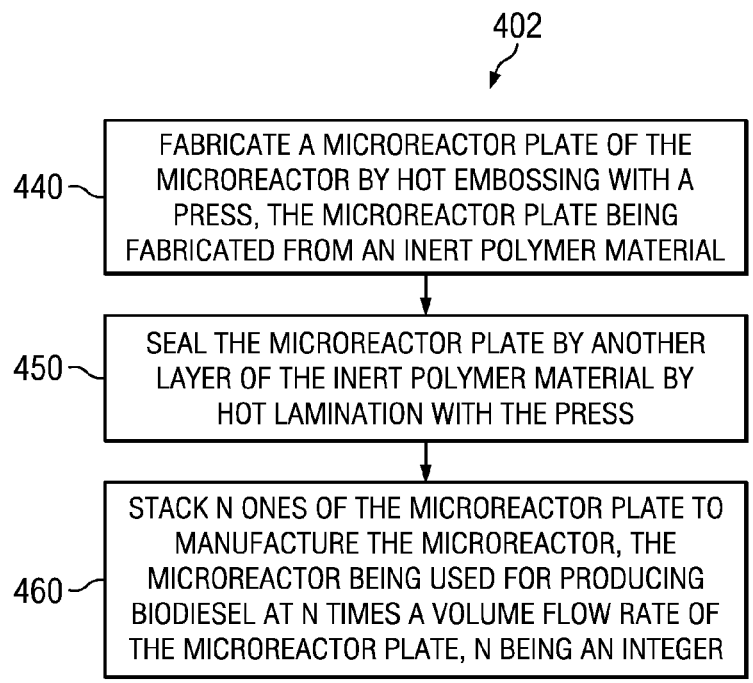
FIG. 4B illustrates a flowchart of a method for fabricating a microreactor, according to some embodiments.

FIG. 4B illustrates a flowchart of a method 402 for fabricating a microreactor, according to some embodiments. In some embodiments, the method 402 is used for manufacturing the microreactors 220 and 250 described with reference to FIGS. 2A-2G. At process 440, a microreactor plate of the microreactor is fabricated by hot embossing with a press, the microreactor plate being fabricated from an inert polymer material, e.g., high-density polyethylene (HDPE). At process 450, the microreactor plate is sealed by another layer of the inert polymer material by hot lamination with the press. At process 460, N ones of the microreactor plate are stacked to manufacture the microreactor, the microreactor being used for producing biodiesel at N times a volume flow rate of the microreactor plate, N being an integer.

With reference to the methods 400 and 402, it is understood that various steps described above may be added, omitted, combined, altered, or performed in different order. For example, in the method 400, process 404 may be added before process 410 to configure the geometry of a microchannel that is used for the reaction. As another example, in the method 402, at process 450 a gasket material may be used to seal the channels. In this embodiment, the material may not be the same as channels, but is desirable to be inert. In the case of a gasket, the seal may be produced by pushing the gasket and channels together (e.g., in a clamp). This may be performed in process 460 when all the reactor plates are stacked up. It may be desirable to select the gasket material that is somewhat flexible (e.g., stiff rubber) but is non-reactive. If the gasket material is too stiff, then the pressure required to seal the channels may exceed desirable limits to damage the channels. If the gasket material is too soft, it may plug the channels. In some embodiments, the gasket material may be a fluoroelastomer such as Viton (Registered Trademark of DuPont Dow Elastomers) (with Durometer ranging from 75-90) having thicknesses from about 0.017" to about 0.04".

Figure 5:
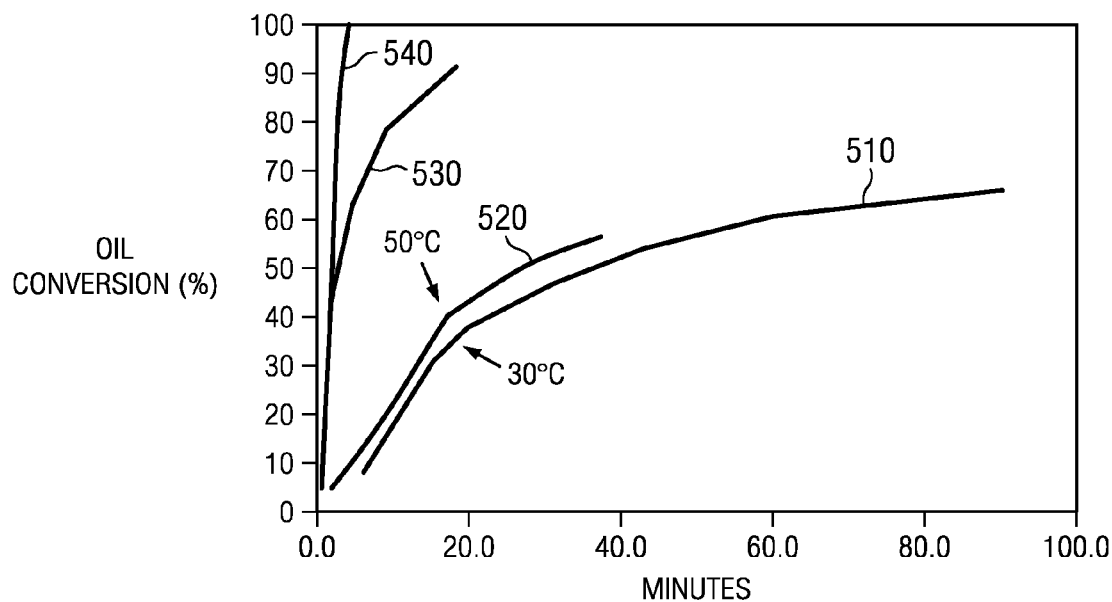
FIG. 5 illustrates in graphical form a comparison of performance of an improved catalytic transesterification process described with reference to FIGS. 1A-1C, 2A-2G, 3A-3D and 4A-4B, and a traditional batch reactor based transesterification process, according to some embodiments.

FIG. 5 illustrates in graphical form, a performance comparison of an improved catalytic transesterification process described with reference to FIGS. 1A-1C, 2A-2G, and 3A-3D, and a traditional batch reactor based transesterification process, according to some embodiments. With oil conversion efficiency shown on the Y-axis in percent, and residence time shown on the X-axis in minutes, graphs 510 and 520 show the performance of a traditional batch reactor, respectively, operating at 30 degrees Celsius and 50 degrees Celsius. For a benchmark residence time of 20 minutes, the traditional batch reactor achieves biodiesel conversion efficiencies that are between 30 and 40%. Graphs 530 and 540 show performance of an improved catalytic transesterification process described with reference to FIGS. 1A, 1B, 1C, 2A, 2B, 2C, and 3 operating at 50 degrees Celsius. For the benchmark residence time of 20 minutes, the improved catalytic transesterification process achieves dramatic improvements in biodiesel conversion efficiencies between 90% and 99.99%.

The improved catalytic transesterification process achieves dramatic improvements in biodiesel conversion efficiencies relative to the traditional batch reactor based conversion process since the improved process generates laminar slug flow, thereby avoiding the generation of microemulsions. A traditional batch reactor facilitates intense stirring of the reactants to produce a microemulsion. The resulting methanol droplet may have much smaller volume (diameters on the order of microns or less) than the laminar slug flow segments, and hence, may have a much higher surface area. Since there is higher surface area, there is more glycerol in contact with the esters. Since it is an interface reaction, it may be desirable to reduce the surface area. Consequently, the formation of microemulsion may be desirable for making the forward reaction go fast (more surface area); however, the increased surface area also enhances the reverse reaction as well. Therefore, formation of microemulsion by intense stirring may lead to a more incomplete reaction due to increased reverse reaction. In addition, if too much catalyst or high free fatty acids are present, there may be a large amount of soaps produced. These soaps act as a surfactant and may create a stable microemulsion of glycerol in esters that may be difficult to separate by gravity separation. The improved method avoids the formation of soaps since the creation of microemulsion is avoided. In the improved method, the esters come out of the microreactor very low in glycerol since it has already been absorbed by the methanol phase. The methanol/glycerol phase may be heavier than the esters and they may immediately fall to the bottom of the collection vessel. Therefore, the improved process may require much less settling time than the traditional batch reactor based methods that use intense mixing.

Several advantages are achieved by the system according to the illustrative embodiments presented herein. The embodiments advantageously provide an improved catalytic transesterification process by using a turbulence free segmented flow pattern having features such as high volume biodiesel production by using a stacked arrangement of modules, low capital and operating costs, low residence times by using a continuous microreactor, compact and modular process equipment design that enables operation in remote areas, farms, and developing countries, low to moderate operating conditions for the process, and low energy usage.

Although illustrative embodiments have been shown and described, a wide range of modification, change and substitution is contemplated in the foregoing disclosure and in some instances, some features of the embodiments may be employed without a corresponding use of other features. Those of ordinary skill in the art will appreciate that the hardware and methods illustrated herein may vary depending on the implementation. For example, while certain aspects of the present disclosure have been described in the context of using vegetable oil, animal fat, or a combination thereof, those of ordinary skill in the art will appreciate that the apparatus and system disclosed herein are capable of being implemented using any biolipids. As another example, it is understood that the specific means for achieving a segmented flow pattern within a microchannel may vary depending on the application requirements and cost considerations.

The methods and systems described herein provide for an adaptable implementation. Although certain embodiments have been described using specific examples, it will be apparent to those skilled in the art that the invention is not limited to these few examples. The benefits, advantages, solutions to problems, and any element(s) that may cause any benefit, advantage, or solution to occur or become more pronounced are not to be construed as a critical, required, or an essential feature or element of the present disclosure.

The above disclosed subject matter is to be considered illustrative, and not restrictive, and the appended claims are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for producing biodiesel, the method comprising:
    dispersing a first reactant and a second reactant to form a laminar slug flow pattern including a first slug of the first reactant and a second slug of the second reactant, the first reactant and the second reactant being immiscible;
    mixing the first reactant and the second reactant to trigger a reaction producing the biodiesel and glycerol, the mixing being convection-enhanced by shear stress induced circulation occurring within each of the first slug of the first reactant and the second slug of the second reactant; and
    separating the glycerol from the biodiesel, the separating occurring simultaneously with the mixing.

2. The method of claim 1, wherein the mixing occurs in a turbulence free flow environment.

3. The method of claim 1, wherein the dispersing is performed in accordance to a configurable proportion of the first reactant and the second reactant.

4. The method of claim 1, wherein the dispersing of the first reactant and the second reactant is performed in a microchannel.

5. The method of claim 1, wherein the second reactant includes alcohol and a catalyst.

6. The method of claim 5, wherein the catalyst is selectable to be one of an acid and a base chemical.

7. The method of claim 1, wherein the first reactant is a biolipid.

8. The method of claim 1, wherein the dispersing of the first reactant and the second reactant occurs in a sequence to form slugs of the first reactant alternating with slugs of the second reactant in a direction of flow.

9. The method of claim 1, wherein the mixing and the separating occurs under a pressure that is less than 5 psi and under a temperature that is less than 70 degrees Celsius.

10. The method of claim 1, wherein a residence time for collecting the biodiesel is configurable as a function of microchannel geometry and the reaction.

11. The method of claim 10, wherein the residence time is configurable to be between 30 seconds and 20 minutes.

12. The method of claim 4, wherein the microchannel has been formed on a first microreactor plate fabricated from an inert polymer material, wherein the first microreactor plate has been sealed by a layer of a second material.

13. The method of claim 12, wherein the inert polymer material and the second material are both high density polyethylene.

14. The method of claim 12, wherein the inert polymer material is high density polyethylene and the second material is a fluoroelastomer.

15. The method of claim 4, wherein the microchannel has a cross section that is square.

16. The method of claim 15, wherein the square cross section of the microchannel has sides between 300 and 700 micrometers in length.

17. The method of claim 4, wherein the microchannel has a cross section that is circular.

18. The method of claim 1, further comprising:
performing the mixing step a second time, on unreacted portions of the first reactant and second reactant; and
performing the separating step a second time, on the glycerol and the biodiesel produced by the second mixing step.

19. The method of claim 1, further comprising:
performing the mixing step a second time, on unreacted portions of the first reactant and second reactant and on a new supply of the first reactant and the second reactant; and
performing the separating step a second time, on the glycerol and the biodiesel produced by the second mixing step.

20. The method of claim 1, further comprising:
recovering the glycerol using an evaporator.

21. The method of claim 1, wherein the shear stress induced circulation comprises vortices in the clockwise and counterclockwise directions, respectively, occurring within each of the first slug of the first reactant and the second slug of the second reactant.

22. The method of claim 1, wherein the method is performed as a continuous flow process.

23. The method of claim 4, wherein the microchannel has configurable dimensions, and a dimension of the microchannel is configurable to be between 300 micrometers and 700 micrometers.

24. The method of claim 4, further comprising:
configuring the geometry of the microchannel.

25. The method of claim 4, wherein the microchannel includes one or more bends along a length thereof.

* * * * *